(12) United States Patent
Zhang et al.

(10) Patent No.: US 9,708,229 B2
(45) Date of Patent: Jul. 18, 2017

(54) CATALYST FOR PREPARING ISOBUTENE BY DISSOCIATION OF METHYL TERT-BUTYL ETHER, PREPARATION METHOD AND USE THEREOF

(71) Applicants: CHINA PETROLEUM & CHEMICAL CORPORATION, Beijing (CN); FUSHUN RESEARCH INSTITUTE OF PETROLEUM AND PETROCHEMICALS, SINOPEC, Fushun, Liaoning (CN)

(72) Inventors: Shumei Zhang, Liaoning (CN); Kai Qiao, Liaoning (CN); Ming Chen, Liaoning (CN); Qingtong Zhai, Liaoning (CN); Changxin Guo, Liaoning (CN); Chunmei Wang, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, SINOPEC, Fushun, Liaoning (CN)

( * ) Notice: Subject to any disclaimer, the term of this patent is extended or adjusted under 35 U.S.C. 154(b) by 438 days.

(21) Appl. No.: 14/353,366

(22) PCT Filed: Oct. 24, 2012

(86) PCT No.: PCT/CN2012/083397
§ 371 (c)(1),
(2) Date: Apr. 22, 2014

(87) PCT Pub. No.: WO2013/060262
PCT Pub. Date: May 2, 2013

(65) Prior Publication Data
US 2014/0275683 A1 Sep. 18, 2014

(30) Foreign Application Priority Data

Oct. 25, 2011 (CN) .......................... 2011 1 0325817
Oct. 25, 2011 (CN) .......................... 2011 1 0325820

(51) Int. Cl.
| | | |
|---|---|---|
| C07C 1/22 | (2006.01) | |
| C07C 1/20 | (2006.01) | |
| B01J 29/035 | (2006.01) | |
| B01J 29/06 | (2006.01) | |
| B01J 35/10 | (2006.01) | |

(52) U.S. Cl.
CPC ............... *C07C 1/22* (2013.01); *B01J 29/035* (2013.01); *B01J 29/0354* (2013.01); *B01J 29/0356* (2013.01); *B01J 29/06* (2013.01); *B01J 35/1019* (2013.01); *B01J 35/1038* (2013.01); *B01J 35/1042* (2013.01); *C07C 1/20* (2013.01); *B01J 2029/062* (2013.01); *B01J 2229/186* (2013.01); *C07C 2521/12* (2013.01); *C07C 2529/035* (2013.01); *C07C 2529/06* (2013.01)

(58) Field of Classification Search
CPC ..................................... C07C 1/20; C07C 1/22
See application file for complete search history.

(56) References Cited

U.S. PATENT DOCUMENTS 4,403,044 A * 9/1983 Post ....................... B01J 29/035
518/713

FOREIGN PATENT DOCUMENTS

| CN | 1684767 A | 10/2005 | |
|---|---|---|---|
| CN | 1853772 A | 11/2006 | |
| FR | 2894851 A1 * | 6/2007 | ............. B01J 29/06 |
| FR | 2894975 A1 | 6/2007 | |

OTHER PUBLICATIONS

Machine translation Fr 2894851. Jun. 22, 2007.*
Machine translation CN 1853772. Nov. 1, 2006.*

* cited by examiner

*Primary Examiner* — Sharon Pregler
*Assistant Examiner* — Alyssa L Cepluch
(74) *Attorney, Agent, or Firm* — Novick, Kim & Lee, PLLC; Allen Xue

(57) ABSTRACT

Disclosed is a catalyst for preparing isobutene by dissociation of methyl tert-butyl ether, the catalyst comprising amorphous silica alumina and a silicalite-1 molecular sieve, wherein the total IR acid amount of weak acids in the catalyst is in a range from 0.020 to 0.080 mmol/g, and the ratio of B acid/L acid of the weak acids is in a range from 2.5:1 to 4.0:1. Also provided is a method of preparing the catalyst and the use thereof. The catalyst has a high selectivity with respect to isobutene, and high conversion of methyl tert-butyl ether, and can also effectively inhibit formation of the by-product dimethyl ether.

14 Claims, No Drawings

CATALYST FOR PREPARING ISOBUTENE BY DISSOCIATION OF METHYL TERT-BUTYL ETHER, PREPARATION METHOD AND USE THEREOF

TECHNICAL FIELD

The present disclosure relates to a catalyst for preparing isobutene by dissociation of methyl tert-butyl ether, and preparation method thereof.

TECHNICAL BACKGROUND

Isobutene is an important organic chemical material, and high purity isobutene is widely used for producing products such as butyl rubbers, polyisobutenes, and so on. Among numerous preparation methods, the method for preparing high purity isobutene by dissociation of methyl tert-butyl ether (MTBE) is advanced in technology and economy. The by-product dimethyl ether in dissociation of MTBE is the main factor that affects purity of the product isobutene. When the product isobutene is used for producing butyl rubbers, there are strict requirements on the content of dimethyl ether. Therefore, the core of this technology is to develop catalysts that can secure high dissociation conversion of MTBE and excellent selectivity of isobutene, with as little as possible or even no generation of dimethyl ether, so as to reduce burden on subsequent separation in MTBE crackers.

Currently, catalysts used for dissociation of MTBE with better performances are alumina catalysts, silica catalysts, ion exchange resin catalysts (as disclosed in DE 3509292A1, DE 3210435A1, U.S. Pat. No. 4,447,668A, GB 1482883A, U.S. Pat. No. 4,570,026A, and U.S. Pat. No. 4,551,567A), sulfate catalysts (as disclosed in JP7626401), active carbon catalysts (as disclosed in JP 7494602), solid phosphoric acid catalysts (as disclosed in CN 96123535.7 and EP 0118085A1), etc.

Comprehensive consideration from the aspects of activity, stability, possibility of regeneration, cost of the catalysts, and so on, arrives at a fact that adopting alumina or silica catalysts for dissociation of MTBE is a preferred selection. When alumina catalysts are used, owing to existence of a large amount of alumina, the catalyst activity is decreased, and therefore a high reaction temperature is required. Especially, methanol generated in the dissociation would be dehydrated under the reaction conditions to produce dimethyl ether, which does not only reduce a yield of methanol, but also negatively affect separation of the products.

In order to reduce or eliminate generation of dimethyl ether, selecting suitable catalysts such as silica based catalysts, or catalysts containing both alumina and silica, is the main approach for reducing by-products of MTBE dissociation, in addition to adopting water injection technology in the reaction process.

The catalysts disclosed in CN 96115213.3 are prepared by calcining silica gel at a temperature in a range from 350 to 550° C. for 1 to 6 h, and then hydrothermally treating the silica gel at a temperature in a range from 200 to 400° C. with saturated steam for 1 to 6 h. Under the reaction conditions of a temperature in a range from 180 to 260° C., a pressure in a range from 0.1 to 0.8 MPa, and an MTBE WHSV (weight hourly space velocity) in a range from 2 to 6 h$^{-1}$, the catalysts can lead to high conversion of MTBE and high selectivity of isobutene, but at the same time with an amount of the by-product dimethyl ether being 0.30%.

In an article titled "Research and Development of Catalysts for Preparing Isobutene by Dissociation of MTBE" (Liu Fusheng, et al.), under "Silica catalytic system" (see *Speciality Petrochemicals,* 1997, No. 4, Pages 1 to 4), it discloses that when a silica based catalyst is adopted, the catalyst hardly has any catalytic activity in case of silica being separately used. However, although addition of a small amount of alumina or modification of the catalyst with a small amount of alumina can increase activity and selectivity of the silica catalyst, the purities of silica raw materials will significantly influence performances of the catalyst. For example, WO 8700166A1 discloses obtaining modified catalysts by impregnating soluble aluminum salt solutions on a high purity silicon oxide, and then drying and calcining the resulting mixture.

An article titled "Preparation of High Purity Isobutene by Dissociation of MTBE" (see *Journal of Fuel Chemistry and Technology,* 2003, Vol. 31, No. 2, Pages 156 to 160) presents a silica-alumina catalyst with a silica amount ranging from 79 wt % to 89 wt %, an alumina amount ranging from 9 wt % to 12 wt %, and an amount of other additives ranging from 10 wt % to 12 wt %. This silica-alumina catalyst is prepared by the following method: firstly, a silica-alumina sol is prepared and neutralized with ammonia water, which is then added with promoters after being aged and eliminated impurities by washing; next, a resulting mixture obtained in the first step is treated (the treating steps are not disclosed herein), molded, dried, and calcined at 850° C. to obtain the catalyst. In the above-mentioned method, the calcining temperature is higher than 700° C., so that the activity and selectivity of the catalyst can reach an optimal state. When the calcining temperature is lower than 700° C., reaction activity of side reactions such as isobutene polymerization or methanol dehydrating of the obtained catalyst, and the like would be increased and thus affect selectivity of the catalyst. In addition, depositions of polymers in the by-products can also affect service life of the catalyst.

CN 1853772A discloses a modified silica-alumina catalyst used for preparation of isobutene by dissociation of MTBE and preparation thereof. This catalyst is obtained by treating amorphous silica-alumina with saturated steam. Because of a smaller specific surface area of the amorphous silica-alumina used separately and a relatively high amount of the L acid of the weak acid, not only improvement of reactivity and selectivity of the catalyst can be affected, but also the content of the by-product dimethyl ether in dissociation of MTBE is still very high.

SUMMARY OF THE INVENTION

To overcome the deficiencies in the prior art, the present disclosure provides a catalyst for preparing isobutene by dissociation of MTBE. The catalyst can substantially decrease generation of the by-product dimethyl ether while keeping an excellent conversion of MTBE and a high selectivity of isobutene and methanol. The present disclosure also relates to a preparation method of the catalyst and use thereof.

According to one aspect of the present disclosure, it provides a catalyst for preparing isobutene by dissociation of MTBE, the catalyst comprising amorphous silica-alumina and a silicalite-1 molecular sieve, wherein a total IR acid amount of weak acids in the catalyst is in a range from 0.020 to 0.080 mmol/g, and the ratio of B acid/L acid is in a range from 2.5:1 to 4.0:1.

The total IR acid amount of weak acids according to the present disclosure refers to the difference between the total IR acid amount measured at 160° C. and the total IR acid amount measured at 250° C. The ratio of B acid/L acid of weak acids refers to the ratio of the difference between the amount of B acid measured at 160° C. and the amount of B acid measured at 250° C. to the difference between the amount of L acid measured at 160° C. and the amount of L acid measured at 250° C. The total IR acid amount, B acid, and L acid are measured by infrared spectroscopy, pyridine being used as a probe molecule. The total IR acid amount and the ratio of B acid/L acid (molar ratio) of the present disclosure both are acid amounts of weak acids.

In the above-mentioned catalyst, the mass ratio of amorphous silica-alumina to silicalite-1 is in a range from 9.5:1 to 1:1, preferably from 9:1 to 4:1.

In the above-mentioned catalyst, in the amorphous silica-alumina, the content of $SiO_2$ is in a range from 60 wt % to 99 wt %, preferably from 80 wt % to 95 wt %, and more preferably from 87 wt % to 93 wt %; and the content of $Al_2O_3$ is in a range from 1 wt % to 40 wt %, preferably from 5 wt % to 20 wt %, and more preferably from 7 wt % to 13 wt %.

In the above-mentioned catalyst, the silicalite-1 molecular sieve is an all-silicon molecular sieve free of aluminium, which has MFI structures, special ten-membered channel structures, and good heat stability, chemical stability, and hydrophobicity.

In the above-mentioned catalyst, the catalyst further comprises an active metal component which is at least one selected from the group consisting of group IIA metals and group VIII metals. The content of the active metal component in the catalyst, based on the active metal element, is in a range from 0.3 wt % to 2.0 wt %. The group IIA metals are at least one selected from Be, Mg, and Ca; and the group VIII metals are at least one selected from Ni, Pd, and Pt.

In the above-mentioned catalyst, the specific surface area of said catalyst is in a range from 240 $m^2$/g to 400 $m^2$/g, and the pore volume of said catalyst is in a range from 0.3 mL/g to 0.8 mL/g.

In the above-mentioned catalyst, the specific surface area is measured according to ASTM D3663-2003 by adopting the low temperature liquid nitrogen adsorption method, and the pore volume is measured according to ASTM D4222-2003 by adopting the low temperature liquid nitrogen adsorption method. The purities of raw materials and compositions of products of the present disclosure are analyzed by adopting gas chromatography.

According to another aspect of the present disclosure, it further provides a method for preparing the above-mentioned catalyst, comprising:

Step a: mixing amorphous silica-alumina with a silicalite-1 molecular sieve, or mixing silica gel and alumina gel with a crystalization solution of the silicalite-1 molecular sieve, and drying and calcining the resulting mixture after molding; and Step b: performing a hydrothermal treatment to the materials obtained in Step a to obtain the catalyst.

In the above method, in step a, the amorphous silica-alumina can be prepared by adopting conventional processes in the prior art, such as a co-precipitation process, a substep precipitation process, and a mechanical mixing process. Generally, the calcining temperature for preparing amorphous silica-alumina is lower than 700° C., preferably in a range from 200 to 600° C. The amorphous silica-alumina used in the present disclosure may also be obtained by calcining silica-alumina gel used as raw materials at the temperature in a range from 200 to 600° C. for 3 to 8 h. The properties of the amorphous silica-alumina are as follows: a specific surface area in a range from 240 $m^2$/g to 450 $m^2$/g, and a pore volume in a range from 0.4 to 0.9 mL/g, preferably, a specific surface area in a range from 270 to 410 $m^2$/g, and a pore volume in a range from 0.5 to 0.7 mL/g.

In the above method, in step a, the weights of silica gel, alumina gel, and crystalization solution of the silicalite-1 molecular sieve, are calculated on a dry basis, i.e., silica gel based on $SiO_2$, alumina gel based on $Al_2O_3$, and the crystallization solution of the silicalite-1 molecular sieve based on $SiO_2$. The weight ratio of the total weight of silica gel and alumina gel to the crystalization solution of the silicalite-1 molecular sieve is in a range from 9.5:1 to 1:1, preferably from 9:1 to 4:1; and the weight ratio of silica gel to alumina gel is in a range from 60:40 to 99:1, preferably from 80:20 to 95:5, and more preferably from 87:13 to 93:7. Silica sol is adopted as the silica gel. The alumina gel can be alumina sol prepared by conventional processes, for example one or more selected from the group consisting of the aluminium chloride process, aluminium nitrate process, aluminium sulfate-sodium metaaluminate process, and sodium metaaluminate-carbon dioxide process.

In the above method, in Step a, the silicalite-1 molecular sieve or the crystalization solution of the silicalite-1 molecular sieve can be synthesized by using a hydrothermal process. Specific steps are as follows: at room temperature, a TPAOH solution with a concentration of 20 to 40 wt % is added into tetraethoxysilane, or a silica sol with a silica concentration of 20 to 30 wt % is mixed with tetrapropylammonium bromide and sodium hydroxide. The above mixed slurry is stirred at a temperature in a range from 70 to 90° C. for 2 to 4 h, and then crystallized for 36 to 96 h at a temperature in a range from 140 to 160° C. and a self-generated pressure, to obtain the crystalization solution of the silicalite-1 molecular sieve. The obtained crystalization solution of the silicalite-1 molecular sieve is taken out to be cooled, separated, washed, dried at a temperature from 90 to 120° C. for 2 to 6 h, and calcined at a temperature from 450 to 600° C. for 2 to 6 h, to obtain the silicalite-1 molecular sieve. The silicalite-1 molecular sieve has a specific surface area in a range from 300 to 400 $m^2$/g, and a pore volume in a range from 0.15 to 0.20 mL/g. The silicalite-1 molecular sieve is in the form of an all-silicon molecular sieve that is free of aluminium and has an MFI structure.

In the above method, the mixing described in Step a can be carried out by adopting the mechanical mixing process, and the molding can be carried out by adopting forming processes, such as preforming, extruding, ball-rolling, and so on. In Step a, the drying can be performed at a temperature from 90 to 120° C. for 2 to 5 h, and the calcining can be performed at a temperature from 450 to 600° C. for 3 to 6 h.

In one example of the above method, in Step b, the temperature of the treatment with saturated steam is in a range from 100 to 600° C., preferably, from 100 to 300° C., and the time of the treatment with saturated steam is in a range from 1 to 10 h, preferably, from 4 to 8 h. After the hydrothermal treatment, the catalyst of the present disclosure is preferably to be obtained by drying steps, which are carried out at a temperature in a range from 90 to 120° C. for 2.0 to 6.0 h.

In the above method, compounds containing active metal components are added in Step a or Step b. The process through which the compounds containing active metal components can be incorporated into the catalyst may include one or more selected from impregnation processes and mixing processes. The impregnation processes may include the saturated impregnation process, spray impregnation process, supersaturated impregnation process, and so on. The active metal components are at least one selected from the group consisting of group IIA metals and group VIII metals. The group IIA metals are at least one selected from the group consisting of Be, Mg, and Ca. The group VIII metals are at least one selected from the group consisting of Ni, Pd, and Pt. The mixing process can be adopted in case of addition in Step a. For example, the compounds containing active metal components can be added in the form of a solid or solution in Step a, to be mixed with the amorphous silica-alumina and silicalite-1 molecular sieve, or with silica gel, alumina gel, and the crystalization solution of the silicalite-1 molecular sieve, followed by being molded, dried, and calcined. Alternately, the impregnation process also can be adopted. For example, the materials obtained by molding in Step a can be dipped into an aqueous solution containing soluble active metal salts, and then dried and calcined. The soluble active metal salts may be nitrates or halides. The impregnation process may be adopted in case of addition in Step b. For example, the materials after the hydrothermal treatment can be dipped into an aqueous solution containing soluble active metal salts, dried at a temperature from 90 to 120° C. for 2 to 6 h, and calcined at a temperature from 200 to 600° C. for 3 to 8 h, to prepare the catalyst.

According to another aspect of the present disclosure, it further provides a method for preparing isobutene by dissociation of MTBE, the method comprising dissociation of MTBE in the presence of the above catalyst to prepare isobutene.

In the above method, the reaction conditions include a liquid hourly space velocity of MTBE in a range from 0.7 to 6.0 $h^{-1}$, a liquid hourly space velocity of water in a range from 0 to 1.0 $h^{-1}$, a temperature in a range from 180 to 360° C., and a pressure ranging from atmospheric pressure to 1.0 MPa, preferably, a liquid hourly space velocity of MTBE in a range from 2.0 to 4.0 $h^{-1}$, a liquid hourly space velocity of water in a range from 0.1 to 0.5 $h^{-1}$, a temperature in a range from 210 to 270° C., and a pressure ranging from atmospheric pressure to 0.6 MPa.

In the present disclosure, the catalyst prepared by mixing silica gel, alumina gel, and the crystalization solution of the silicalite-1 molecular sieve to be followed by molding and the hydrothermal treatment is preferably loaded with a proper amount of active metal components. The catalyst can be used for preparing isobutene by dissociation of MTBE. The catalyst exhibits better catalytic performances with good selectivity of methanol and isobutene, and high conversion of MTBE. Furthermore, the catalyst can better restrain generation of the by product dimethyl ether.

In the present disclosure, the silicalite-1 molecular sieve used is an all-silicon molecular sieve free of aluminium, and has an MFI structure, and good heat stability, chemical stability, and hydrophobicity. However, in silica-alumina molecular sieves, such as Y type molecular sieves, β molecular sieves, ZSM-5 molecular sieves, the presence of aluminium thereof does not only influence the catalyst acid property, but also increases hydrophilicity of the catalyst, which is disadvantageous to MTBE dissociation reactions.

In the catalyst of the present disclosure, composition of the all-silicon silicalite-1 molecular sieve and amorphous silica-alumina can improve acid strength and acid distribution of the catalyst, and facilitate further adjustment of acid properties of the catalyst by the hydrothermal treatment owning to coordination between the silicalite-1 molecular sieve and the amorphous silica-alumina, which will result in more B acid sites and less L acid sites of weak acids of the catalysts, that is, a higher ratio of B acid/L acid of weak acids. In another aspect, the composition of the all-silicon silicalite-1 molecular sieve and amorphous silica-alumina can improve the pore structure of the catalyst, which promotes diffusion of MTBE and the dissociation products. Additionally, the hydrothermal treatment of the method provided by the present disclosure can improve polarity on the catalyst surface, particularly polarity on the surface of the silicalite-1 molecular sieve, so that hydrophobicity and lipophilicity of the catalyst surface can be stronger, which can obviously weaken capacity of water adsorption while making both adsorption of the reactants and desorption of the products easier. The introduction of active metal components into the catalyst can further increase the total amount of weak acids in the catalyst and the ratio of B acid/L acid, thus improvinge properties of the catalyst, and reducing generation of the by-product dimethyl ether as well.

The catalyst of the present disclosure shows outstanding catalytic performances in the preparation of isobutene by dissociation of MTBE. It does not only improve dissociation activity of MTBE and selectivity of the product isobutene, but also decreases generation of the by-product dimethyl ether.

DETAILED DESCRIPTION OF EMBODIMENTS

The present disclosure will be explained in detail in connection with the following examples, which are not to restrict the scope of the present disclosure in any manner.

Specific measurement of a total IR acid, B acid, and L acid of the present disclosure is performed according to an existing IR acidity measurement method (see *Catalyst Analysis*, pages 90 to 92, published by Northeastern University Press in July, 2000). Specific steps are as follows:

1. Preparation of a sample: 20 mg of a finely grinded sample (particle size lower than 200 mesh) is measured, crushed into a sheet with a diameter of 20 mm, and placed into an infrared absorption cell; another 200 mg of the sample (sheet) is loaded into a hanging cup at a lower end of a quartz spring; the system is evacuated to $1\times10^{-2}$ Pa, heated to 500° C., and maintained for 1 h; the sample is purified, removed of adsorbates, water, and so on that cover the surface of the sample.

2. The system is cooled down to room temperature under the above evacuated conditions, and after absorbing pyridine for 5 min, is heated up to 160° C., and balanced for 1 h; the pyridine physically absorbed is desorbed; the total acid amount is acquired by utilizing the pyridine gravimetric absorption method, and the infrared spectrum obtained under the above-mentioned method is recorded, wherein the band that corresponds to B acid is 1,545 $cm^{-1}$, and the band that corresponds to L acid is 1,455 $cm^{-1}$; therefore the total acid amount, B acid amount, and L acid amount at 160° C. can be obtained.

3. The temperature is kept raising till 250° C., and balanced for 1 h; the pyridine physically absorbed is desorbed, and the infrared spectrum obtained under the above-mentioned method is recorded; the total acid amount is acquired by utilizing the pyridine gravimetric absorption method, and the infrared spectrum obtained under the above-mentioned method is recorded, wherein the band that corresponds to B acid is 1,545 $cm^{-1}$, and the band that corresponds to L acid is 1,455 $cm^{-1}$; therefore the total acid amount, B acid amount, and L acid amount at 250° C. can be obtained.

Example 1

Preparation of the Catalyst

Silica-alumina gel with a silicon-alumina weight ratio of 92.0:8.0 based on $SiO_2$ and $Al_2O_3$ is used as the raw material, which is calcined for 4 h under 450° C. to obtain amorphous silica-alumina SA, with a specific surface area of 277 m²/g, a pore volume of 0.59 mL/g, a $SiO_2$ content of 92.0 wt %, and an $Al_2O_3$ content of 8.0 wt %.

At room temperature, a TPAOH (tetrapropylammonium hydroxide) solution with a concentration of 30 wt % is added to tetraethyl orthosilicate. The resulting mixed slurry is stirred at 80° C. for 3 h and taken out after being crystallized for 48 h at 150° C. The crystallized resultant is then calcined for 4 h at 550° C. to obtain an all-silicon molecular sieve, i.e., silicalite-1, with a specific surface area of 333 m²/g and a pore volume of 0.17 mL/g.

The amorphous silica-alumina SA is mixed with the silicalite-1 molecular sieve in a weight ratio of 9:1, ball-rolled for molding, dried under 110° C. for 3 h, and then calcined at 500° C. for 4 h. After that, the resulting materials are treated with saturated steam at 200° C. for 5 h, dried at 110° C. for 3 h to obtain a catalyst C-1. The characterization data of the catalyst are shown in Table 1.

Preparation of Isobutene by Dissociation of MTBE

The study of corresponding dissociation reactions is carried out in a microreactor. The reaction conditions comprise an LHSV of MTBE being 2.5 h$^{-1}$, an LHSV of water being 0.5 h$^{-1}$, a temperature of 225° C., and a pressure of 0.2 MPa. The test results are shown in Table 2.

Example 2

The method of Example 1 is repeated except that the amorphous silica-alumina SA and the silicalite-1 molecular sieve are mixed in a weight ratio of 4 to 1 to obtain a catalyst C-2, the data of which are shown in Table 1. The result data of corresponding dissociation reactions are shown in Table 2.

Example 3

The method of Example 1 is repeated except that the amorphous silica-alumina SA and the silicalite-1 molecular sieve are mixed in a weight ratio of 1 to 1, and that the amorphous silica-alumina SA has a $SiO_2$ content of 83.0 wt %, an $Al_2O_3$ content of 17.0 wt %, a specific surface area of 320 m²/g, and a pore volume of 0.61 mL/g. The data of an obtained catalyst C-3 are shown in Table 1. The result data of corresponding dissociation reactions are shown in Table 2.

Example 4

The method of Example 3 is repeated except that the amorphous silica-alumina SA and the silicalite-1 molecular sieve are mixed in a weight ratio of 5 to 1. The data of an obtained catalyst C-4 are shown in Table 1. The result data of corresponding dissociation reactions are shown in Table 2.

Example 5

The method of Example 1 is repeated except that the saturated impregnation method is adopted, in which the materials after being treated with steam and dried are immerged into an aqueous solution of nickel chloride and magnesium chloride, and then dried at 110° C. for 3 h to obtain a catalyst C-5, the data of which are shown in Table 1. The result data of corresponding dissociation reactions are shown in Table 2.

Example 6

The method of Example 2 is repeated except that the saturated impregnation method is adopted, in which the materials after being treated with steam and dried are immerged into an aqueous solution of palladium nitrate and calcium chloride, and then dried at 110° C. for 3 h to obtain a catalyst C-6, the data of which are shown in Table 1. The result data of corresponding dissociation reactions are shown in Table 2.

Example 7

The method of Example 2 is repeated except that the amorphous silica-alumina SA and the silicalite-1 molecular sieve are mixed with beryllium oxide, wherein the dosage of beryllium oxide base on beryllium is 1.8 wt %. The data of an obtained catalyst C-7 are shown in Table 1. The result data of corresponding dissociation reactions are shown in Table 2.

Example 8

Silica sol, alumina sol, and a crystallization solution Si-1-A of the silicalite-1 molecular sieve are mixed in a weight ratio of 10:1:5 on a dry basis, ball-rolled for molding, dried at 110° C. for 3 h, and then calcined at 500° C. for 4 h. Next, the obtained materials are treated with saturated steam at 300° C. for 4 h, and then dried at 110° C. for 3 h to obtain a catalyst C-8. The data representing the catalyst are shown in Table 1. The molecular sieve crystallization solution Si-1-A is prepared by the following method. At room temperature, the TPAOH solution with a concentration of 30 wt % is added to TEOS. The resulting mixed slurry is stirred at 80° C. for 3 h and then taken out after being crystallized for 48 h at 150° C. to obtain the crystallization solution Si-1-A of the silicalite-1 molecular sieve.

The study of dissociation reactions is carried out on a microreactor. The reaction conditions comprise a liquid hourly space velocity of MTBE being 2.0 h$^{-1}$, a liquid hourly space velocity of water being 0.5 h$^{-1}$, a temperature of 200° C., and a pressure of the atmospheric pressure. The result data of the dissociation reactions are shown in Table 2.

Example 9

The method of Example 8 is repeated except that the silica sol and alumina sol are mixed with the crystallization solution Si-1-A of the silicalite-1 molecular sieve in a weight ratio of 15:2:4 on a dry basis. The data of an obtained catalyst C-9 are shown in Table 1.

Example 10

The method of Example 8 is repeated except that the silica sol and alumina sol are mixed with the crystallization solution Si-1-A of the silicalite-1 molecular sieve in a weight ratio of 10:1:2 on a dry basis. The data of an obtained catalyst C-10 are shown in Table 1. The result data of the dissociation reactions are shown in Table 2.

Example 11

The method of Example 8 is repeated except that the silica sol and alumina sol are mixed with the crystalization solution Si-1-A of the silicalite-1 molecular sieve in a weight ratio of 40:3:10 on a dry basis. The data of an obtained catalyst C-11 are shown in Table 1.

Example 12

The method of Example 9 is repeated except that the saturated impregnation method is adopted, in which the materials after being treated with steam and dried are immerged into an aqueous solution of nickel chloride and magnesium chloride, and then dried at 110° C. for 3 h to obtain a catalyst C-12, the data of which are shown in Table 1. The result data of corresponding dissociation reactions are shown in Table 2.

Example 13

The method of Example 9 is repeated except that the saturated impregnation method is adopted, in which the materials after being treated with steam and dried are immerged into an aqueous solution of palladium nitrate and calcium chloride, and then dried at 110° C. for 3 h to obtain a catalyst C-13, the data of which are shown in Table 1.

Example 14

The method of Example 10 is repeated except that the saturated impregnation method is adopted, in which the materials after being treated with steam and dried are immerged into an aqueous solution of palladium nitrate, and then dried at 110° C. for 3 h to obtain a catalyst C-14, the data of which are shown in Table 1. The result data of corresponding dissociation reactions are shown in Table 2.

Example 15

The method of Example 11 is repeated except that the saturated impregnation method is adopted, in which the materials after being treated with steam and dried are immerged into an aqueous solution of beryllium nitrate, and then dried at 110° C. for 3 h to obtain a catalyst C-15, the data of which are shown in Table 1. The result data of corresponding dissociation reactions are shown in Table 2.

Example 16

The method of Example 8 is repeated except that the silica sol and alumina sol are mixed with the crystalization solution Si-1-A of the silicalite-1 molecular sieve, and magnesium oxide, wherein the dosage of magnesium oxide based on magnesium is 1.8 wt %, and the weight ratio of silica sol to alumina sol to the crystalization solution Si-1-A of the silicalite-1 molecular sieve is, on a dry basis, 20:2:3. A catalyst C-16 is obtained, the data of which are shown in Table 1. The result data of corresponding dissociation reactions are shown in Table 2.

Comparative Example 1

The method of Example 1 is repeated except that the steam treatment is not performed, and the data of an obtained catalyst H-1 are shown in Table 1. The result data of corresponding dissociation reactions are shown in Table 2.

Comparative Example 2

The method of Example 9 is repeated except that the steam treatment is not performed, and the data of an obtained catalyst H-2 are shown in Table 1. The result data of corresponding dissociation reactions are shown in Table 2.

Comparative Example 3

The method of Example 5 is repeated except that the catalyst is free of the silicalite-1-A molecular sieve. The data of an obtained catalyst H-3 are shown in Table 1. The result data of corresponding dissociation reactions are shown in Table 2.

Comparative Example 4

The method of Example 9 is repeated except that the raw materials free of the crystalization solution of the silicalite-1-A molecular sieve comprise the silicon sol and the alumina sol, and that the saturated impregnation method is adopted, in which the materials after being treated with steam and dried are immerged into a solution of nickel chloride and magnesium chloride, and then dried at 110° C. for 3 h to obtain a catalyst H-4. The data are shown in Table 1.

The study of corresponding dissociation reactions is carried out in a microreactor. The reaction conditions are the same as those of Example 9. The data of the dissociation reactions are shown in Table 2.

TABLE 1

| | Catalyst | | | | | | |
|---|---|---|---|---|---|---|---|
| | Catalyst | Silica-alumina to molecular sieve wt:wt | Total acid content * mmol/g | B acid/L acid * | Specific surface area m$^2$/g | Pore volume mL/g | Active metal, based on metals wt % |
| Example 1 | C-1 | 9:1 | 0.058 | 3.14 | 280 | 0.56 | 0 |
| Example 2 | C-2 | 4:1 | 0.055 | 2.76 | 292 | 0.53 | 0 |
| Example 3 | C-3 | 1:1 | 0.049 | 2.75 | 313 | 0.54 | 0 |
| Example 4 | C-4 | 5:1 | 0.054 | 2.77 | 306 | 0.59 | 0 |
| Example 5 | C-5 | 9:1 | 0.061 | 3.15 | 265 | 0.53 | Ni 1.2, Mg 0.5 |
| Example 6 | C-6 | 4:1 | 0.058 | 2.78 | 290 | 0.55 | Pd 0.2, Ca 0.5 |
| Example 7 | C-7 | 4:1 | 0.057 | 3.16 | 272 | 0.50 | Be 1.8 |

TABLE 1-continued

| | Catalyst | Silica-alumina to molecular sieve wt:wt | Total acid content * mmol/g | B acid/L acid * | Specific surface area m²/g | Pore volume mL/g | Active metal, based on metals wt % |
|---|---|---|---|---|---|---|---|
| Example 8 | C-8 | 11:5 | 0.060 | 2.93 | 290 | 0.49 | 0 |
| Example 9 | C-9 | 17:4 | 0.059 | 2.96 | 301 | 0.51 | 0 |
| Example 10 | C-10 | 11:2 | 0.053 | 2.87 | 320 | 0.57 | 0 |
| Example 11 | C-11 | 43:10 | 0.054 | 3.11 | 293 | 0.55 | 0 |
| Example 12 | C-12 | 17:4 | 0.057 | 2.98 | 286 | 0.48 | Ni 1.2, Mg 0.5 |
| Example 13 | C-13 | 17:4 | 0.054 | 2.97 | 288 | 0.50 | Pd 0.2, Ca 0.5 |
| Example 14 | C-14 | 11:2 | 0.054 | 2.89 | 310 | 0.55 | Pt 0.25 |
| Example 15 | C-15 | 43:10 | 0.055 | 3.11 | 274 | 0.55 | Be 1.8 |
| Example 16 | C-16 | 22:3 | 0.052 | 2.79 | 307 | 0.52 | Mg 1.8 |
| Comparative Example 1 | H-1 | 9:1 | 0.091 | 0.28 | 289 | 0.54 | 0 |
| Comparative Example 2 | H-2 | 17:4 | 0.051 | 0.29 | 298 | 0.50 | 0 |
| Comparative Example 3 | H-3 | — | 0.071 | 2.16 | 260 | 0.65 | Ni 1.2, Mg 0.5 |
| Comparative Example 4 | H-4 | — | 0.039 | 1.83 | 256 | 0.63 | Ni 1.2, Mg 0.5 |

* Note:
The total acid content described in Table 1 refers to the total IR acid content of weak acids, and the B acid/L acid described in Table 1 refers to the ratio of B acid/L acid of weak acids.

Comparative Example 5

Amorphous silica-alumina SA is mixed with a molecular sieve ZSM-5 (the molar ratio of silica to alumina is 95 to 5) in a weight ratio of 9 to 1, ball-rolled for molding, dried at 110° C. for 3 h, and then calcined at 500° C. for 4 h, to obtain a catalyst H-5. The result data of corresponding dissociation reactions are shown in Table 2.

Comparative Example 6

The catalyst H-5 obtained in Comparative Example 5 is treated with saturated steam at 200° C. for 5 h and then dried at 110° C. for 3 h to obtain a catalyst H-6. The result data of corresponding dissociation reactions are shown in Table 2.

TABLE 2

Data of dissociation of MTBE for preparing isobutene

| catalysts | | Conversion of MTBE, wt. % | Selectivity of isobutene, wt. % | Content of dimethyl ether in the products, wt. % |
|---|---|---|---|---|
| Example 1 | C-1 | 99.9 | 99.9 | 0.27 |
| Example 2 | C-2 | 99.9 | 99.9 | 0.27 |
| Example 3 | C-3 | 99.9 | 99.9 | 0.29 |
| Example 4 | C-4 | 99.9 | 99.9 | 0.25 |
| Example 5 | C-5 | 99.9 | 99.9 | 0.20 |
| Example 6 | C-6 | 99.9 | 99.9 | 0.19 |
| Example 7 | C-7 | 99.9 | 99.9 | 0.21 |
| Example 8 | C-8 | 99.9 | 99.9 | 0.28 |
| Example 10 | C-10 | 99.9 | 99.9 | 0.24 |
| Example 12 | C-12 | 99.9 | 99.9 | 0.21 |
| Example 14 | C-14 | 99.9 | 99.9 | 0.19 |
| Example 15 | C-15 | 99.9 | 99.9 | 0.23 |
| Example 16 | C-16 | 99.9 | 99.9 | 0.27 |
| Comparative Example 1 | H-1 | 87.2 | 99.9 | 0.40 |
| Comparative Example 2 | H-2 | 89.0 | 99.9 | 0.37 |
| Comparative Example 3 | H-3 | 99.6 | 99.8 | 0.39 |
| Comparative Example 4 | H-4 | 99.7 | 99.8 | 0.36 |
| Comparative Example 5 | H-5 | 80.2 | 96.5 | 0.44 |
| Comparative Example 6 | H-6 | 85.1 | 97.8 | 0.41 |

It can be seen from Table 2 that using the catalyst of the present disclosure comprising amorphous silica-alumina and the silicalite-1 molecular sieve for preparing isobutene by dissociation of MTBE, not only can improve conversion of MTBE and selectivity of isobutene, but also can make an obvious effect on decreasing the by-product dimethyl ether compared with the prior art. This illustrates that the catalyst of the present disclosure has a higher level of activity and selectivity. At the same time, addition of active metal components can effectively control side reactions and thus further reduce the content of the by-product dimethyl ether.

The invention claimed is:

1. A method for preparing isobutene by a dissociation reaction of methyl tert-butyl ether (MTBE), comprising:
   contacting a feedstock with a catalyst in a reactor; and
   obtaining an effluent from the reactor,
   wherein the feedstock comprises MTBE and water,
   wherein the effluent comprises an isobutene product stream, and wherein the catalyst comprises amorphous silica alumina and a silicalite-1 molecular sieve.

2. The method of claim 1, wherein a liquid hourly space velocity of MTBE in the reactor is in a range from 0.7 to 6.0 $h^{-1}$, a liquid hourly space velocity of water in the reactor is in a range from 0 to 1.0 $h^{-1}$, a temperature in the reactor is in a range from 180 to 360° C., and a pressure in the reactor is in a range from the atmospheric pressure to 1.0 MPa.

3. The method of claim 2, wherein the liquid hourly space velocity of MTBE is in a range from 2.0 to 4.0 $h^{-1}$, the liquid hourly space velocity of water is in a range from 0.1 $h^{-1}$ to 0.5 $h^{-1}$, the temperature is in a range from 210 to 270° C., and the pressure is in a range from the atmospheric pressure to 0.6 MPa.

4. The method of claim 1, wherein the catalyst has a total IR acid amount of weak acids in a range from 0.020 to 0.080 mmol/g, and a ratio of B acid/L acid of the weak acids is in a range from 2.5:1 to 4.0:1.

5. The method of claim 1, wherein the catalyst a mass ratio of the amorphous silica-alumina to the silicalite-1 is in a range from 9.5:1 to 1:1.

6. The method of claim 5, wherein the mass ratio of the amorphous silica-alumina to the silicalite-1 is in a range from 8:1 to 4:1.

7. The method of claim 1, wherein in said amorphous silica-alumina, a content of $SiO_2$ is in a range from 60 wt % to 99 wt %, and a content of $Al_2O_3$ is in a range from 1 wt % to 40 wt %.

8. The method of claim 7, wherein in said amorphous silica-alumina, the content of silica is in a range from 80 wt % to 95 wt %, and the content of alumina is in a range from 5 wt % to 20 wt %.

9. The method of claim 1, wherein the catalyst further comprises an active metal component selected from the group consisting of Group IIA metals and Group VIII metals.

10. The method of claim 9, wherein a content of said active metal component, calculated based on elemental metal, is in a range from 0.3 wt % to 2.0 wt % of a total weight of the catalyst.

11. The method of claim 10, the active metal component is selected from the group consisting of Be, Mg, Ca, Ni, Pd, and Pt.

12. The method of claim 1, wherein the isobutene product comprises less that 0.30 wt % of dimethyl ether.

13. The method of claim 1, wherein a selectivity of isobutene of the MTBE dissociation reaction is about 99.9%.

14. The method of claim 1, wherein a conversion of MTBE in the MTBE dissociation reaction is about 99.9%.

* * * * *